United States Patent [19]

Barberet et al.

[11] Patent Number: Plant 5,580

[45] Date of Patent: Nov. 5, 1985

[54] CARNATION NAMED LONTRELOS

[75] Inventors: Nicole Barberet; Yves Ducloux, both of Antibes, France

[73] Assignee: Laboratoire de Physiologie Vegetale de La Londe, Antibes, France

[21] Appl. No.: 516,567

[22] Filed: Jul. 25, 1983

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new spray carnation variety particularly distinguished by the very light Orient Pink coloration of its blossoms which are borne on straight, rather rigid peduncles branching from a rather rigid, upright stem having rather abundant foliage and a vigorous, upright growth habit which is rather resistant to *Fusarium oxysporum.*

1 Drawing Figure

BACKGROUND OF THE NEW PLANT

Our new spray carnation is the result of breeding efforts carried on by us at La Londe, Les Maures, France, since 1973 with the object of developing a plant having nice color and good quality of flower stem and plant growth habit, and particularly resistant to *Fusarium oxysporum*. This new plant originated as a seedling produced by our crossing of selected and individually identified plants growing among stock of spray carnations maintained at La Londe for breeding purposes and this particular seedling was selected by us for propagation and test because of its very delicate pink coloration, its very favorable growth habit and its apparent resistance to *Fusarium oxysporum*. This discovery plant was produced by us at La Londe, by means of cuttings, with such a favorable result with respect to retention of the novel characteristics of its parent that we continued such propagation through several successive generations over a period of years and thereby determined that the novel and distinctive characteristics of the discovery plant weer fully retained from generation to generation and appeared to be firmly fixed.

DESCRIPTION OF THE DRAWING

Our new spray carnation is illustrated by the accompanying photographic drawing which shows, in full color, the upper portion of a typical flowering stem with buds and flowers in various stages of opening, the colors shown being as nearly true to those specified herein as is reasonably possible to obtain by conventional photographic procedures.

DESCRIPTION OF THE NEW PLANT

The following is a detailed description of our new spray carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—Stock Plant No. 7 V 6.

*Pollen parent.*—Stock Plant No. 9 M B 1. These unnamed varieties are individually identified in our permanent records and are maintained in our spray carnation collection for breeding purposes at La Londe, France.

Classification:

*Botanic.*—*Dianthus caryophyllus.*

*Commercial.*—Spray Carnation.

Form: Tall, erect bush with at least four stems emitted near the ground.

Height: Averaging about 110 cm. at eight months.

Main stem:

*Length.*—Less than 15 cm. due to pinching.

Branching character: Moderately branched from all stems.

Growth habit: Vigorous, upright and rather rigid.

Foliage:

*Quantity.*—Rather abundant.

*Number of Leaves.*—At least 120.

*Leaf size.*—About 13 cm. long and 9 mm. wide, in average at the seventh node.

*Leaf shape.*—Linear with rolled margin.

*Texture.*—Leathery.

*Color.*—Upper side — 188A. Under side — 188A.

*Ribs and veins.*—Hardly noticeable.

*Rachis.*—Hardly noticeable.

THE BUD

Form: Ovoid.

Size:

*Diameter.*—About 1.2 cm.

*Length.*—About 2.5 cm.

Rate of opening: Normal for carnations.

Color of petals:

*When sepals first divide.*—A little darker than at full bloom.

*When petals begin to unfurl.*—A little darker than at full bloom.

Sepals:

*Number.*—Five.

*Shape.*—Joined at lower part with the upper part of acute form and sharply pointed at the apex. The sepals are hooded over the bud and stand up when the flowers open.

*Color.*—Inside — Greenish white. Outside — 139C and 144D.

*Striae.*—Longitudinal.

Calyx:

*Shape.*—Slightly bell-shaped and long.

*Splitting.*—The calyx does not split.

*Aspect.*—Smooth.

Flower stem:

*Length.*—About 60 cm.

*Character.*—Erect and rather thin.

*Color.*—188A.

THE FLOWER

Blooming habit: Recurrent, blooming profusely during midseason of Spring and Fall.

Size of bloom: Small.

*Diameter.*—Averaging about 6 cm.

*Depth.*—Averaging about 4.5 cm.

Borne: In cluster.

Shape:

*When bloom first opens.*—High centered.

*When bloom matures.*—Dome-shaped.

Petalage:

*Number of petals.*—About 28 in average.

*Arrangement.*—Imbricated.

*Form.*—Fan-shaped with wavy or undulated edge.

*Texture.*—Soft.

*Appearance.*—Satiny.

*Color.*—Outer Petal: Body — 36B and 36C. Base — Yellowish green. Reverse side — 36D. Inside Petal: Body — 36B and 36C. Base — Yellowish green. Reverse side — 36D.

Flower stem:

*Length.*—About 60 cm.

*Character.*—Upright and of good strength.

*Color.*—188A.

Fragrance: Distinctly perceptible.

Persistence: The flowers hang on and dry.

Lasting quality:

*As cut flower.*—At least ten days in vase keeping.

Disease resistance: Rather resistant to *Fusarium oxysporum* as observed INRA, Antibes, Alpes-Maritimes, France.

REPRODUCTIVE ORGANS

Stamens:

*Number.*—About 15.

*Arrangement.*—Around the pistils.

*Anthers.*—Size: Less than 4 mm. Color: Whitish.

*Filaments.*—Color — Whitish.

Pistils:

*Number.*—Two.

*Styles.*—Color — White.

*Stigmas.*—Color — White.

Character of ovaries: Hardly ribbed and with chlorophyll.

This new variety of spray carnation most resembles "Silvery Pink" but differs from "Silvery Pink" by a more glaucous foliage, a stiffer stem, and a higher degree of earliness. In particular, the new variety is distinguished by its tolerance to *Fusarium oxysporum.*

We claim:

1. A new and distinct spray carnation plant, substantially as herein shown and described, characterized by the very light Orient Pink coloration of its small blooms which are produced profusely on long, straight and strong flowering stems; and by its vigorous and upright growth habit, abundant foliage and resistance to *Fusarium oxysporum.*

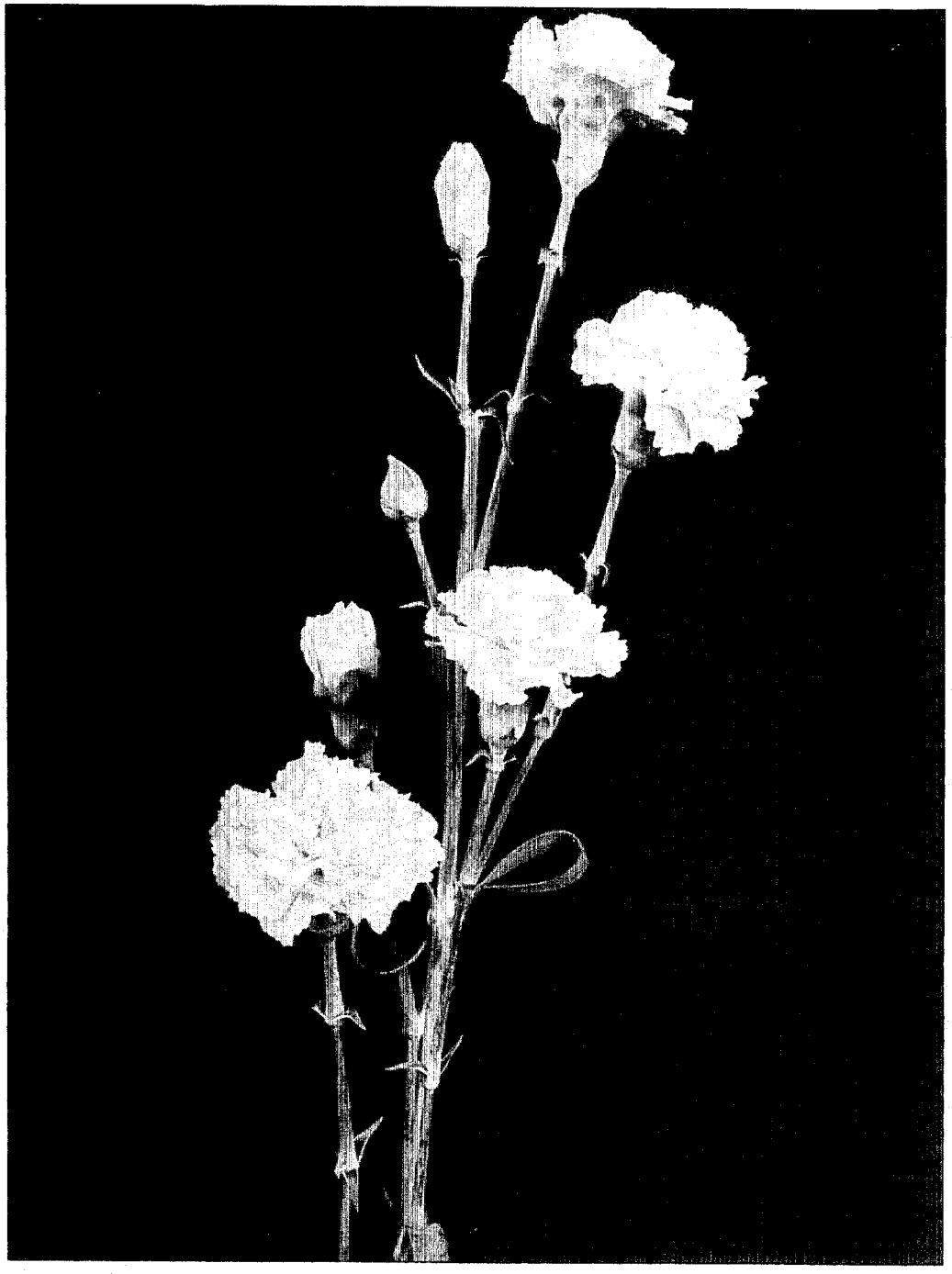

* * * * *